United States Patent
Goodman et al.

(10) Patent No.: US 9,717,571 B2
(45) Date of Patent: *Aug. 1, 2017

(54) DENTAL ABUTMENT SYSTEM

(71) Applicant: Biomet 3i, LLC, Palm Beach Gardens, FL (US)

(72) Inventors: Ralph E. Goodman, West Palm Beach, FL (US); John J. Bellanca, West Palm Beach, FL (US); Zachary B. Suttin, Jupiter, FL (US); Ross W. Towse, Fort Wayne, IN (US)

(73) Assignee: Biomet 3I, LLC, Palm Beach Gardens, FL (US)

(*) Notice: Subject to any disclaimer, the term of this patent is extended or adjusted under 35 U.S.C. 154(b) by 307 days.

This patent is subject to a terminal disclaimer.

(21) Appl. No.: 14/516,375

(22) Filed: Oct. 16, 2014

(65) Prior Publication Data
US 2015/0044637 A1    Feb. 12, 2015

Related U.S. Application Data

(63) Continuation of application No. 13/238,665, filed on Sep. 21, 2011, now Pat. No. 8,888,486.
(Continued)

(51) Int. Cl.
*A61C 8/00*    (2006.01)

(52) U.S. Cl.
CPC ........... *A61C 8/0068* (2013.01); *A61C 8/006* (2013.01); *A61C 8/0063* (2013.01); *A61C 8/0077* (2013.01)

(58) Field of Classification Search
CPC ... A61C 8/0054; A61C 8/0062; A61C 8/0068; A61C 8/0069; F16B 39/24; F16B 39/26; F16B 43/00
(Continued)

(56) References Cited

U.S. PATENT DOCUMENTS 2,227,464 A    1/1941    Olson
2,270,748 A    1/1942    Baker
(Continued)

FOREIGN PATENT DOCUMENTS

DE    2114323    10/1971
DE    2157139    5/1972
(Continued)

OTHER PUBLICATIONS

International Search Report mailed Jan. 17, 2012 issued in corresponding International Patent Application No. PCT/US2011/051973 (3 pages).
(Continued)

*Primary Examiner* — Cris L Rodriguez
*Assistant Examiner* — Matthew Saunders
(74) *Attorney, Agent, or Firm* — Schwegman Lundberg & Woessner, P.A.

(57) ABSTRACT

A dental implant screw for holding an abutment on a dental implant includes a head and a shaft. A proximal end of the shaft is coupled to the head. The shaft includes a threaded section, an outwardly tapered section leading into a recessed section, and a stop section directly between the outwardly tapered section and the recessed section. The recessed section is directly between the head and the stop section. The threaded section is directly adjacent a distal end of the shaft and is configured to engage threads of an internally threaded bore in the dental implant to hold the abutment on the dental implant.

19 Claims, 9 Drawing Sheets

Related U.S. Application Data

(60) Provisional application No. 61/385,707, filed on Sep. 23, 2010.

(58) Field of Classification Search
USPC .................................................. 433/173, 174
See application file for complete search history.

(56) References Cited

U.S. PATENT DOCUMENTS

| | | | |
|---|---|---|---|
| 2,289,066 A | | 7/1942 | Olson |
| 2,713,883 A | | 7/1955 | Ougljesa |
| 2,721,387 A | | 10/1955 | Ashuckian |
| 3,298,270 A | * | 1/1967 | Launay .................. F16B 39/26 |
| | | | 277/640 |
| 3,732,621 A | | 5/1973 | Bostrom |
| 3,777,796 A | | 12/1973 | Takano |
| 3,958,471 A | | 5/1976 | Muller |
| 4,011,602 A | | 3/1977 | Rybicki |
| 4,177,562 A | | 12/1979 | Miller |
| 4,259,072 A | | 3/1981 | Hirabayashi |
| 4,462,730 A | | 7/1984 | Knohl |
| 4,547,157 A | | 10/1985 | Driskell |
| 4,560,353 A | | 12/1985 | Schulte |
| 4,575,340 A | | 3/1986 | Lustig |
| 4,624,673 A | | 11/1986 | Meyer |
| 4,713,004 A | | 12/1987 | Linkow |
| 4,738,623 A | | 4/1988 | Driskell |
| 4,746,293 A | | 5/1988 | Lundgren |
| 4,756,689 A | | 7/1988 | Lundgren |
| 4,758,161 A | | 7/1988 | Niznick |
| 4,772,204 A | | 9/1988 | Soderberg |
| 4,793,808 A | | 12/1988 | Kirsch |
| 4,824,372 A | | 4/1989 | Jorneus |
| 4,846,683 A | | 7/1989 | Lazzara |
| 4,850,870 A | | 7/1989 | Lazzara |
| 4,850,873 A | | 7/1989 | Lazzara |
| 4,854,872 A | | 8/1989 | Detsch |
| 4,856,994 A | | 8/1989 | Lazzara |
| 4,872,839 A | | 10/1989 | Brajnovic |
| 4,904,187 A | | 2/1990 | Zingheim |
| 4,955,811 A | | 9/1990 | Lazzara |
| 4,958,970 A | | 9/1990 | Rose |
| 4,978,640 A | | 12/1990 | Kelly |
| 4,988,297 A | | 1/1991 | Lazzara |
| 4,988,298 A | | 1/1991 | Lazzara |
| 5,000,686 A | | 3/1991 | Lazzara |
| 5,006,069 A | | 4/1991 | Lazzara |
| 5,011,351 A | * | 4/1991 | Terry ...................... F16B 39/24 |
| | | | 29/525.02 |
| 5,015,186 A | | 5/1991 | Detsch |
| 5,022,860 A | * | 6/1991 | Lazzara ............... A61C 8/0022 |
| | | | 433/174 |
| 5,030,096 A | | 7/1991 | Hurson |
| 5,035,619 A | | 7/1991 | Daftary |
| 5,040,982 A | | 8/1991 | Stefan-Dogar |
| 5,040,983 A | | 8/1991 | Binon |
| 5,049,073 A | | 9/1991 | Lauks |
| 5,064,373 A | | 11/1991 | Staubli |
| 5,071,345 A | | 12/1991 | Rosen |
| 5,071,351 A | | 12/1991 | Green, Jr. |
| 5,073,111 A | | 12/1991 | Daftary |
| 5,082,442 A | | 1/1992 | Rosen |
| 5,087,200 A | | 2/1992 | Brajnovic |
| 5,100,323 A | | 3/1992 | Friedman |
| 5,104,318 A | | 4/1992 | Piche |
| 5,105,690 A | | 4/1992 | Lazzara |
| 5,106,300 A | | 4/1992 | Voitik |
| 5,122,059 A | | 6/1992 | Durr |
| 5,125,839 A | | 6/1992 | Ingber |
| 5,135,395 A | | 8/1992 | Marlin |
| 5,145,371 A | | 9/1992 | Jorneus |
| 5,145,372 A | | 9/1992 | Daftary |
| 5,152,687 A | | 10/1992 | Amino |
| 5,154,612 A | | 10/1992 | Carlsson |
| 5,169,308 A | | 12/1992 | Kvist |
| 5,169,309 A | | 12/1992 | Staubli |
| 5,188,800 A | | 2/1993 | Green, Jr. |
| 5,195,891 A | | 3/1993 | Sulc |
| 5,195,892 A | | 3/1993 | Gersberg |
| 5,197,881 A | | 3/1993 | Chalifoux |
| 5,209,659 A | | 5/1993 | Friedman |
| 5,209,666 A | | 5/1993 | Balfour |
| 5,213,502 A | | 5/1993 | Daftary |
| 5,246,370 A | | 9/1993 | Coatoam |
| 5,281,140 A | | 1/1994 | Niznick |
| 5,282,746 A | | 2/1994 | Sellers |
| 5,286,195 A | | 2/1994 | Clostermann |
| 5,292,252 A | | 3/1994 | Nickerson |
| 5,297,963 A | | 3/1994 | Dafatry |
| 5,308,285 A | | 5/1994 | Malen |
| 5,316,476 A | | 5/1994 | Krauser |
| 5,334,024 A | | 8/1994 | Niznick |
| 5,336,090 A | | 8/1994 | Wilson, Jr. |
| 5,338,196 A | | 8/1994 | Beaty |
| 5,344,457 A | | 9/1994 | Pilliar |
| 5,350,300 A | | 9/1994 | Gallais |
| 5,362,234 A | | 11/1994 | Salazar |
| 5,362,235 A | | 11/1994 | Daftary |
| 5,368,483 A | | 11/1994 | Sutter |
| 5,417,570 A | | 5/1995 | Zuest |
| 5,419,702 A | | 5/1995 | Beaty |
| 5,431,567 A | | 7/1995 | Daftary |
| 5,433,606 A | | 7/1995 | Niznick |
| 5,437,551 A | | 8/1995 | Chalifoux |
| 5,447,435 A | | 9/1995 | Brodbeck |
| 5,476,382 A | | 12/1995 | Daftary |
| 5,476,383 A | | 12/1995 | Beaty |
| 5,482,463 A | | 1/1996 | Wilson, Jr. |
| 5,492,471 A | | 2/1996 | Singer |
| 5,527,183 A | | 6/1996 | O'Brien |
| 5,533,898 A | | 7/1996 | Mena |
| 5,538,426 A | | 7/1996 | Harding |
| 5,547,377 A | | 8/1996 | Daftary |
| 5,564,924 A | | 10/1996 | Kwan |
| 5,571,016 A | | 11/1996 | Ingber |
| 5,588,838 A | | 12/1996 | Hansson |
| 5,622,500 A | * | 4/1997 | Niznick ............... A61C 8/0048 |
| | | | 206/63.5 |
| 5,662,473 A | | 9/1997 | Rassoli |
| 5,685,714 A | | 11/1997 | Beaty |
| 5,699,148 A | | 12/1997 | Shiozawa |
| 5,711,669 A | | 1/1998 | Hurson |
| 5,725,375 A | | 3/1998 | Rogers |
| 5,733,122 A | | 3/1998 | Gordon |
| 5,777,724 A | | 7/1998 | Suzuki |
| 5,782,918 A | | 7/1998 | Klardie |
| 5,816,812 A | | 10/1998 | Kownacki |
| 5,829,977 A | | 11/1998 | Rogers |
| 5,833,463 A | | 11/1998 | Hurson |
| 5,879,161 A | | 3/1999 | Lazzara |
| 5,882,200 A | | 3/1999 | Sutter |
| 5,904,483 A | | 5/1999 | Wade |
| 5,947,732 A | | 9/1999 | Beaty |
| 5,947,733 A | | 9/1999 | Sutter |
| 5,984,680 A | | 11/1999 | Rogers |
| 5,989,026 A | | 11/1999 | Rogers |
| 6,152,737 A | | 11/2000 | Beaty |
| 6,168,435 B1 | | 1/2001 | Beaty |
| 6,217,331 B1 | | 4/2001 | Rogers |
| RE37,227 E | | 6/2001 | Brodbeck |
| 6,287,116 B2 | | 9/2001 | Lazzara |
| 6,343,930 B1 | | 2/2002 | Beaty |
| 6,375,465 B1 | | 4/2002 | Engman |
| 6,394,808 B2 | | 5/2002 | Rizzo |
| 6,394,809 B2 | | 5/2002 | Rogers |
| 6,416,324 B1 | | 7/2002 | Day |
| 6,447,295 B1 | | 9/2002 | Kumar |
| 6,500,003 B2 | | 12/2002 | Nichinonni |
| 6,663,388 B1 | | 12/2003 | Schar |
| 6,743,018 B1 | | 6/2004 | Morrow |
| 6,848,908 B2 | | 2/2005 | Bjorn |
| 6,932,606 B2 | | 8/2005 | Aravena |
| 6,986,660 B2 | | 1/2006 | Kumar |
| 7,300,283 B2 | | 11/2007 | Aravena |

(56) References Cited

U.S. PATENT DOCUMENTS

| | | |
|---|---|---|
| 7,300,284 B2 | 11/2007 | Linder |
| 7,338,286 B2 | 3/2008 | Porter |
| 7,484,959 B2 | 2/2009 | Porter |
| 7,632,095 B2 | 12/2009 | Ostman |
| 8,033,826 B2 | 10/2011 | Towse |
| 8,888,486 B2 * | 11/2014 | Goodman ............ A61C 8/006 433/174 |
| 2004/0101808 A1 | 5/2004 | Porter |
| 2005/0266383 A1 | 12/2005 | Aravena |
| 2009/0130629 A1 | 5/2009 | Towse |
| 2011/0318710 A1 | 12/2011 | Towse |

FOREIGN PATENT DOCUMENTS

| | | |
|---|---|---|
| DE | 2717506 | 5/1978 |
| DE | 3224112 | 2/1984 |
| DE | 3531389 | 3/1987 |
| DE | 3825601 | 3/1989 |
| DE | 4028855 | 3/1992 |
| DE | 4127839 | 3/1992 |
| EP | 0320024 | 6/1989 |
| EP | 0477644 | 4/1992 |
| EP | 0657146 | 6/1995 |
| GB | 1291470 | 10/1972 |
| GB | 1305478 | 1/1973 |
| GB | 2213065 | 8/1989 |
| SU | 1570720 | 6/1990 |
| WO | WO 85/002337 | 6/1985 |

OTHER PUBLICATIONS

International Written Opinion mailed Jan. 17, 2012 issued in corresponding International Patent Application No. PCT/US2011/051973 (9 pages).

"European Application Serial No. 11827266.5, Extended European Search Report mailed Apr. 14, 2016", 8 pgs.

"European Application Serial No. 11827266.5, Response filed Nov. 14, 2016 to Extended European Search Report mailed Apr. 14, 2016", 12 pgs.

* cited by examiner

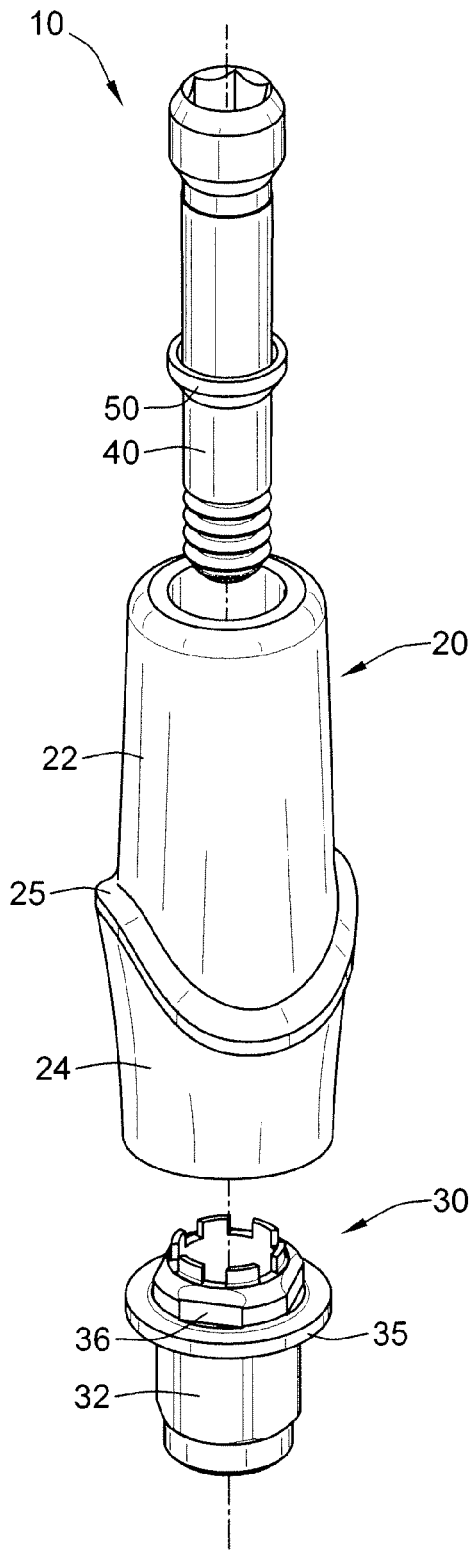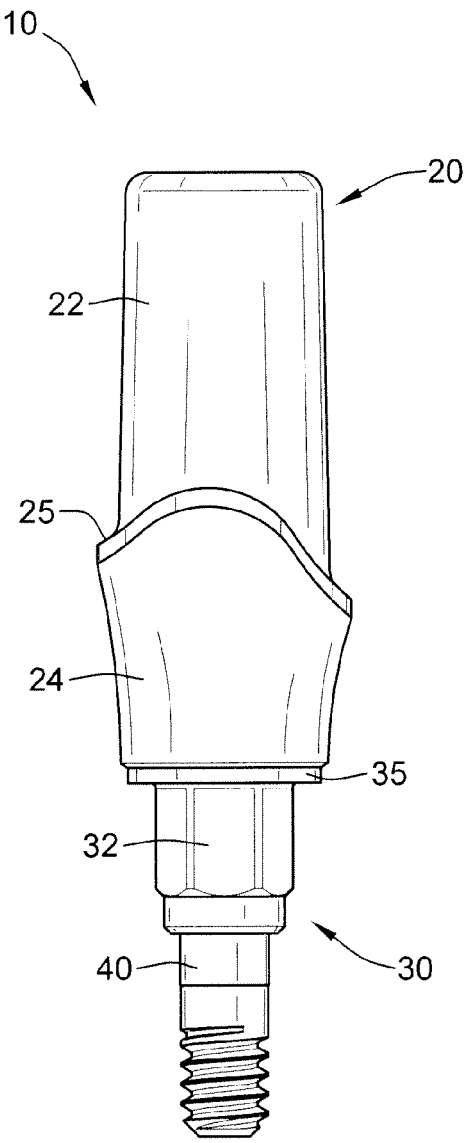
FIG. 1A
FIG. 1B

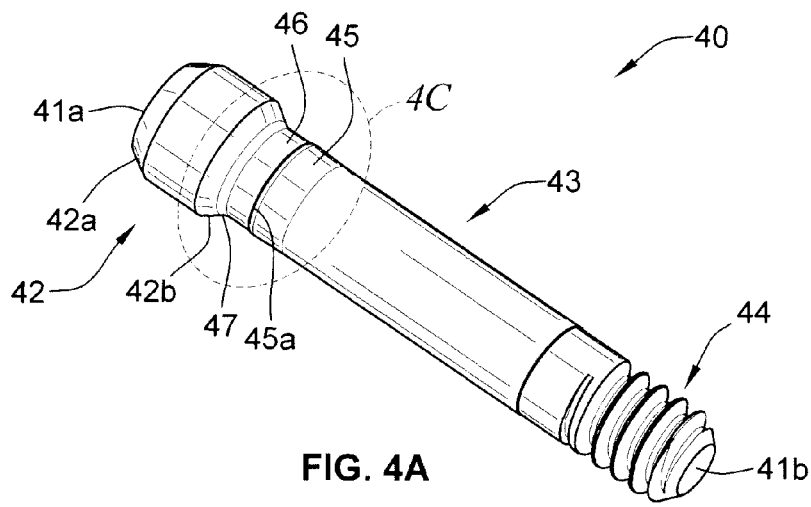
FIG. 4A
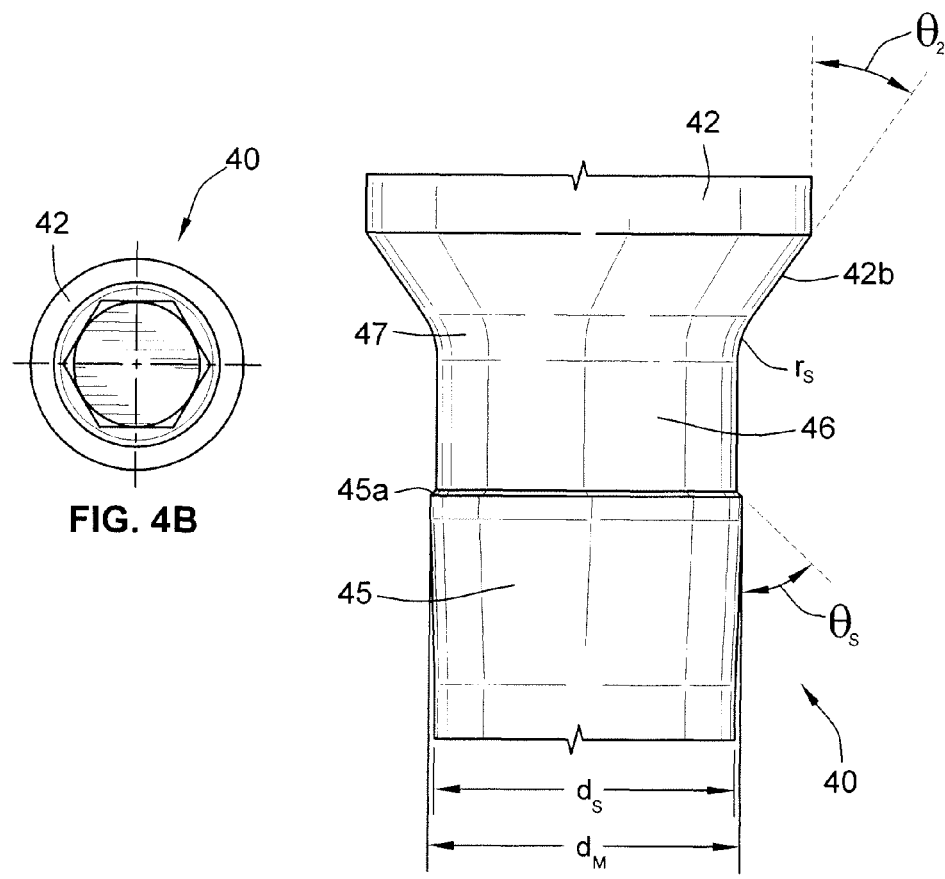
FIG. 4B
FIG. 4C

DENTAL ABUTMENT SYSTEM

CROSS-REFERENCE TO RELATED APPLICATION

This application is a continuation of prior application Ser. No. 13/238,665, filed Sep. 21, 2011, now allowed, which claims the benefit of U.S. Provisional Application No. 61/385,707, filed Sep. 23, 2010, each of which is hereby incorporated by reference herein in its entirety.

FIELD OF INVENTION

The present invention relates generally to dental implant systems. More particularly, the present invention relates to a two-piece abutment system having a screw and a washer.

BACKGROUND OF THE INVENTION

The dental restoration of a partially or wholly edentulous patient with artificial dentition is typically done in two stages. In the first stage, an incision is made through the gingiva to expose the underlying bone. After a series of drill bits creates an osteotomy in the bone, a dental implant is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant preferably has the same general contour as the gingival portion of the natural tooth being replaced.

Once the clinician believes the implant is suitable for receiving a prosthesis, surgical techniques are used to place the dental prostheses by means of an abutment. According to one prior art abutment, the abutment is made from a ceramic material and has an internal bore through which a screw is inserted to hold the abutment on the implant. The internal bore of the ceramic abutment can be very abrasive. While installing the abutment using the screw, the internal bore can scratch and/or deform a seating surface on the head of the screw, which can negatively effect the connection between the abutment and the implant.

The screw may be pretensioned to prevent or minimize the separation between the individual components of a dental implant system, such as, for example, between the abutment and the implant. As a screw is fully threaded into a prethreaded bore in the implant, the screw is tensioned between the engaging threaded surfaces of the screw and the prethreaded bore, and the abutting surfaces of the screw head and a stationary seating surface around the bore in the implant. After the screw head seats on the stationary seating surface, the tension on the screw increases as the screw is threaded farther into the prethreaded bore. This tension on the screw produces a force that is commonly referred to as the "preload" of the screw. Thus, "preload" may be defined as the maximum initial force required to reverse out a tightened screw. Preload may also be described as the clamping force. By reducing the friction between the rotating surfaces of the screw and the opposed stationary surfaces, the preload on the screw can be increased for any applied torque because that torque will cause the screw to be advanced farther into its bore.

SUMMARY OF THE INVENTION

In one aspect, an abutment system for use with a dental implant is described. The dental implant has an internally threaded bore and a non-round fitting located at a gingival end portion thereof. The abutment system includes a prosthetic portion, an insert, a screw, and a washer. The prosthetic portion is configured to support a prosthesis thereon. The prosthetic portion has a supragingival region for protruding beyond gingiva adjacent to the dental implant and a subgingival end. The prosthetic portion has a passageway extending therethrough. The insert extends into the passageway and engages the subgingival end of the prosthetic portion. The insert has a central opening and an anti-rotational feature for engaging the non-round fitting of the dental implant. The screw is configured to engage threads of the internally threaded bore in the dental implant. The screw is insertable through the passageway in the prosthetic portion and the central opening in the insert. The screw includes a head and a shaft. The shaft includes a threaded section, an outwardly tapered section terminating in a stop section, and a recessed section. The stop section is directly adjacent the recessed section. The washer is fitted over the recessed section and has an inner diameter that is less than a maximum diameter of the outwardly tapered section of the shaft.

In another aspect, an abutment system for use with a dental implant is described. The dental implant has an internally threaded bore. The abutment system includes a prosthetic portion, a screw, and a washer. The prosthetic portion is configured to support a prosthesis thereon. The prosthetic portion has a supragingival section for protruding beyond gingiva adjacent to the dental implant and a subgingival section. The prosthetic portion has an internal bore extending therethrough. The screw is configured to engage threads of the internally threaded bore in the dental implant. The screw is insertable through the internal bore in the prosthetic portion. The screw includes a head and a shaft. The shaft includes a threaded section, an outwardly tapered section leading into a recessed section, and a stop section positioned directly between the outwardly tapered section and the recessed section. The washer is positioned about the recessed section. The washer has an inner diameter that is less than a maximum diameter of the outwardly tapered section of the shaft.

In one aspect, a dental implant screw for holding an abutment on a dental implant is described. The dental implant screw includes a head and a shaft. The shaft has a proximal end and a distal end. The proximal end of the shaft is fixedly coupled to the head. The shaft includes a threaded section, an outwardly tapered section leading into a recessed section, and a stop section directly between the outwardly tapered section and the recessed section. The recessed section is directly between the head and the stop section. The threaded section is directly adjacent the distal end of the shaft and is configured to engage threads of an internally threaded bore in the dental implant to hold the abutment on the dental implant.

In another aspect, an abutment system for use with a dental implant is described. The dental implant has an internally threaded bore. The abutment system includes a prosthetic portion, a screw, and a washer. The prosthetic portion is configured to support a prosthesis thereon. The prosthetic portion has an internal bore. The internal bore includes a tapered bore surface having an angle of α degrees relative to a vertical axis parallel with the internal bore of the prosthetic portion. The screw is insertable through the internal bore of the prosthetic portion and is configured to engage threads of the internally threaded bore of the implant. The screw includes a head and a shaft. The head includes a tapered head surface having an angle of substantially α degrees relative to the vertical axis parallel with the internal bore of the prosthetic portion. The washer includes a top tapered washer surface that is configured to engage with the tapered head surface of the screw and a bottom tapered washer surface that is configured to engage with the tapered bore surface of the prosthetic portion. The top and bottom tapered washer surfaces each have an angle of β degrees relative to the vertical axis parallel with the internal bore of the prosthetic portion. β is at least 20 percent greater than α.

BRIEF DESCRIPTION OF THE DRAWINGS

FIG. 1A is an exploded view of a two-piece abutment including a prosthetic portion, an insert, a screw, and a washer;

FIG. 1B is an assembled view of the two-piece abutment of FIG. 1A;

FIG. 4A is a perspective view of the screw of FIG. 1A;

FIG. 4B is a top view of the screw of FIG. 4A;

FIG. 4C is an enlarged partial front view of the screw of FIG. 4A;

Figure 2A:
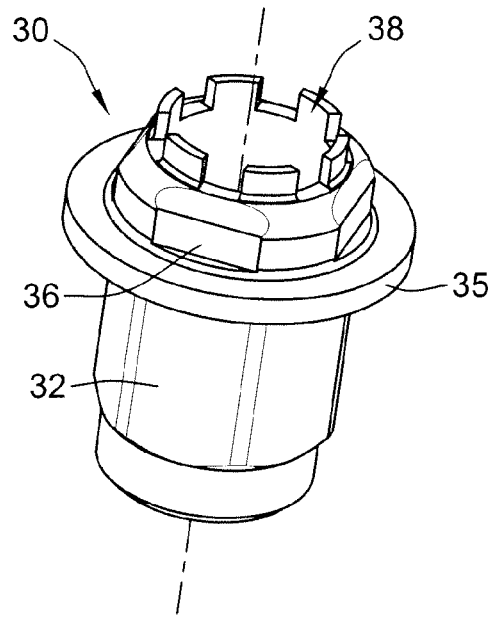
FIG. 2A is a perspective view of the insert of FIG. 1A.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Referring to FIGS. 1A and 1B, a two-piece abutment 10 is illustrated. FIG. 1A is an exploded view of the two-piece abutment 10 and FIG. 1B is an assembled view of the two-piece abutment 10. The two-piece abutment 10 includes a prosthetic portion 20, an insert 30, a screw 40, and a washer 50. The prosthetic portion 20 includes a support or supragingival region 22 and a subgingival region 24. The support region 22 and the subgingival region 24 are separated by a shoulder 25. In operation, tooth-like material, such as porcelain, is formed into the size and shape of a natural tooth and is mounted on the support region 22, interfacing at the shoulder 25. The shoulder 25 is typically just below the gingival tissue.

Figure 6:
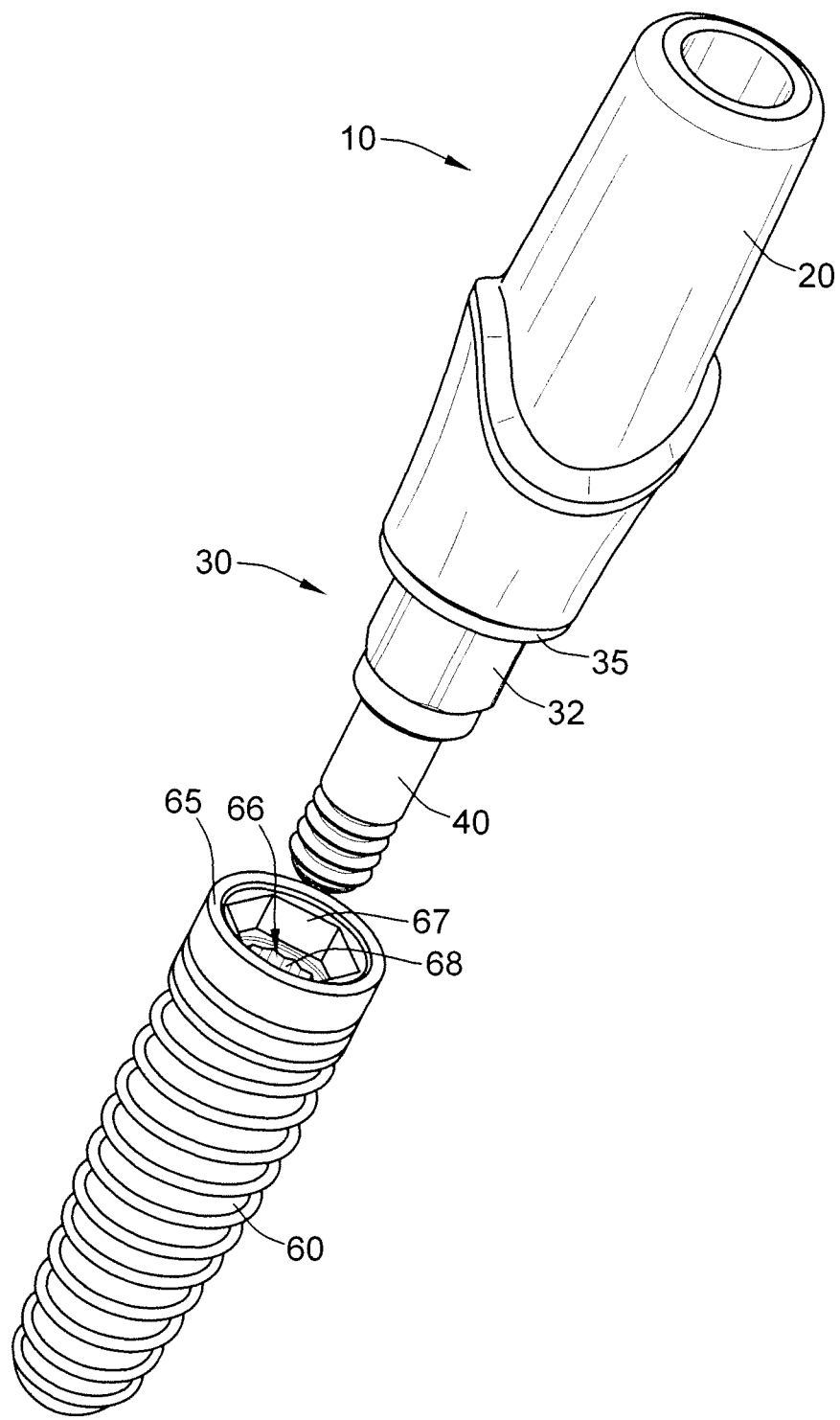
FIG. 6 is a partially exploded perspective view of the assembled two-piece abutment of FIG. 1B and an implant.
Figure 7:
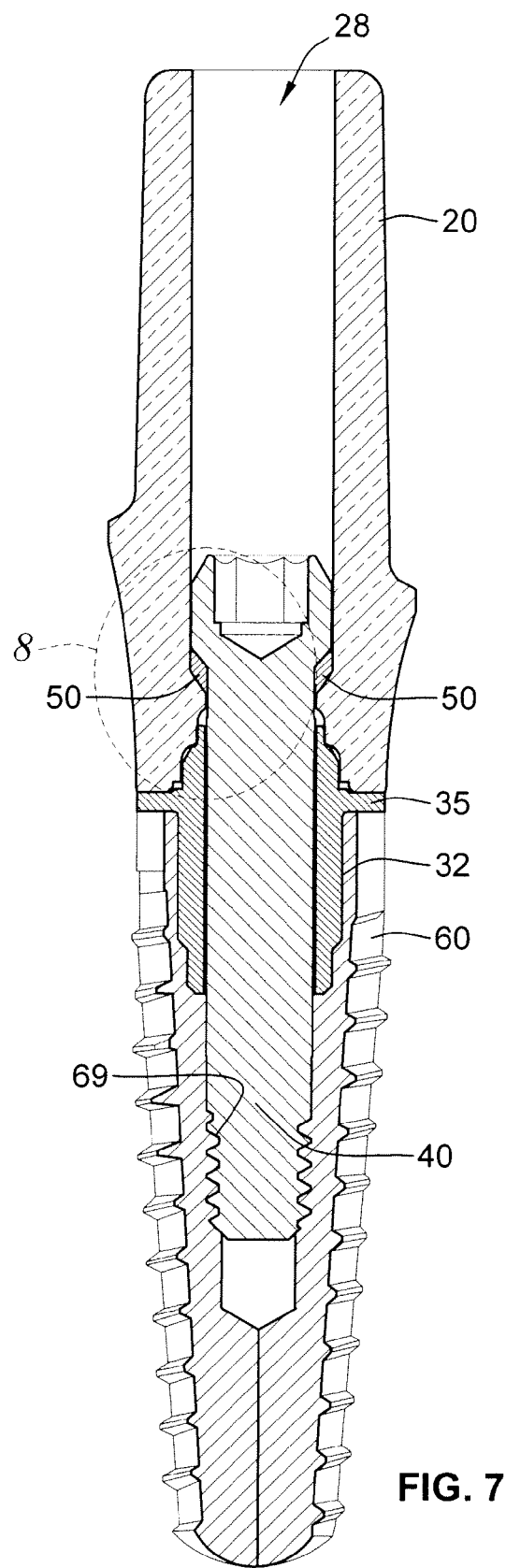
FIG. 7 is a front cross-sectional view of the assembled two-piece abutment of FIG. 1B mated with the implant of FIG. 6.

The insert 30 includes an anti-rotational feature 32 (e.g., a hexagonally shaped region) for non-rotationally mating with an implant 60 (shown in FIGS. 6 and 7). The insert 30 further includes a table 35 that interfaces with the prosthetic portion 20, as shown best in FIG. 1B, and with the implant 60 (shown in FIG. 7). Above the table 35, there is a non-round section 36 (FIG. 1A). The non-round section 36 serves to non-rotationally hold the insert 30 within the prosthetic portion 20.

Figure 2B:
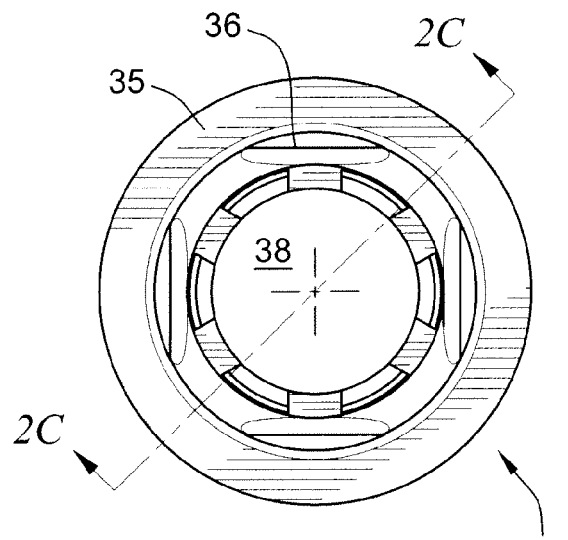
FIG. 2B is a top view of the insert of FIG. 2A.
Figure 2C:
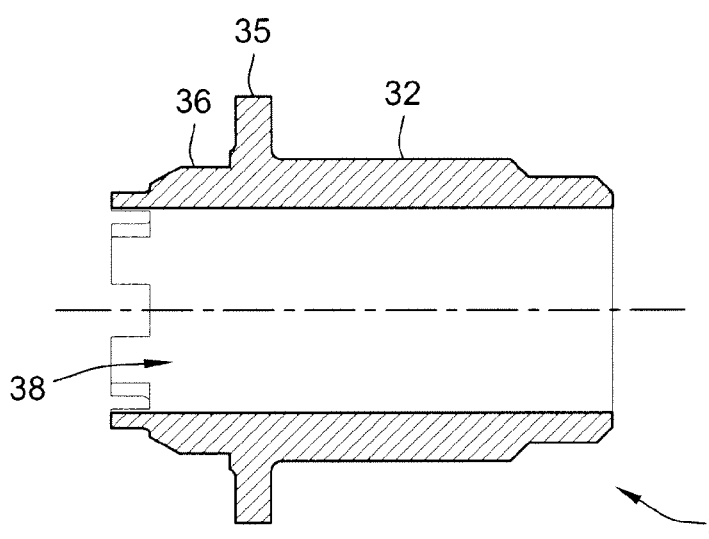
FIG. 2C is a side cross-sectional view of the insert of FIG. 2A.

Referring to FIGS. 2A-2C, the insert 30 generally has a tubular shape due to an internal opening 38 that extends entirely through the insert 30. An upper portion of the insert 30 above the table 35 is for engaging the prosthetic portion 20. A lower portion of the insert 30 below the table 35 is for engaging the implant 60 (shown in FIGS. 6 and 7). In the illustrated embodiment, two opposing surfaces of the non-round section 36 are substantially aligned with two opposing surfaces of the anti-rotational feature 32 as shown in FIG. 2A. However, this is not required as these surfaces can be angularly offset from each other.

Figure 3B:
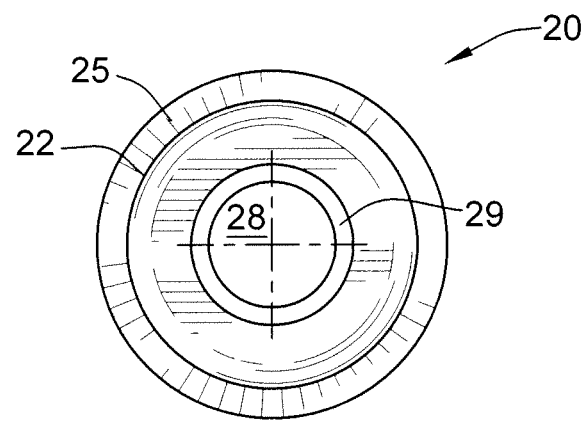
FIG. 3B is a top view of the prosthetic portion of FIG. 3A.
Figure 3A:
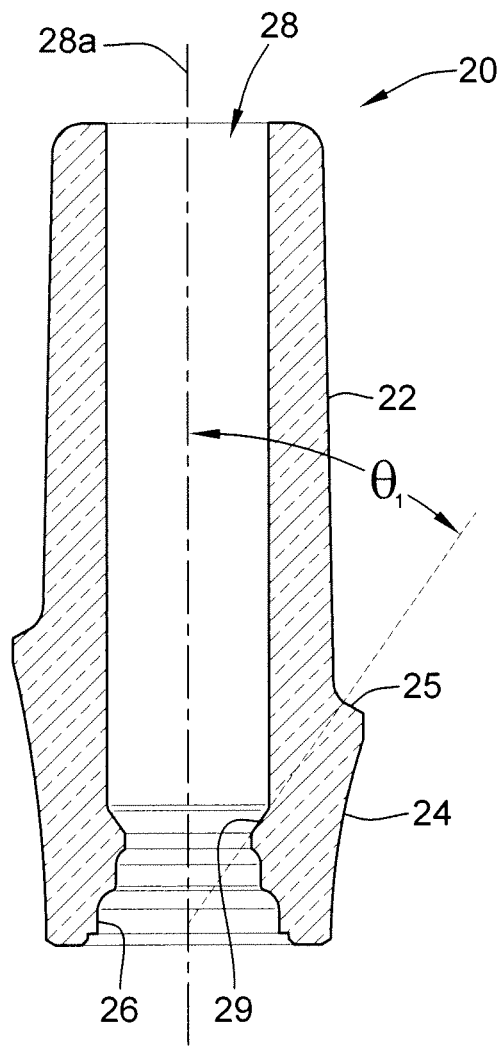
FIG. 3A is a front cross-sectional view of the prosthetic portion of FIG. 1A.

Referring to FIGS. 3A-3B, the prosthetic portion 20 generally has a tubular shape due to an internal bore 28 that extends entirely through the prosthetic portion 20. The internal bore 28 of the prosthetic portion 20 includes a non-round section 26 and a tapered bore surface 29. The tapered bore surface 29 has an angle of $\theta_1$ relative to the vertical. The internal bore 28 has a central axis 28a that is parallel with the vertical. $\theta_1$ can be a variety of angles, such as, for example, about 35 degrees. As will be explained in further details below, the washer 50 is sandwiched between a head 42 of the screw 40 and the tapered bore surface 29 to hold the two-piece abutment 10 on the implant 60 (FIGS. 6 and 7).

The non-round section 26 of the prosthetic portion 20 can be engaged with the non-round section 36 of the insert 30 to resist any rotational movement between the two parts, such as, for example, as shown in FIG. 1B. The non-round section 26 of the prosthetic portion 20 can be manufactured in various shapes and forms, and can be created by tools such as a D-broach, a square broach, or an octagonal broach. As best shown in FIG. 1B, the table 35 of the insert 30 substantially matches the dimension of the lowermost portion of the prosthetic portion 20 such that there is no overhang between the prosthetic portion 20 and the insert 30.

Referring generally to FIGS. 4A-4C, the screw 40 is illustrated. The screw 40 generally includes a head 42 and a shaft 43. The head 42 has a first tapered head surface 42a and a second tapered head surface 42b. The second tapered head surface 42b has an angle of $\theta_2$ relative to the vertical. $\theta_2$ can be a variety of angles, such as, for example, about 35 degrees. It is contemplated that $\theta_2$ is the same as, or similar to, $\theta_1$ (the angle of the tapered bore surface 29). The first and the second tapered head surfaces 42a,b can have the same or different angles. Alternatively, the first tapered head surface 42a can be 90 degrees such that the top of the head 42 is flat (i.e., the first tapered head surface is not tapered surface).

The shaft 43 and the head 42 meet at a transition 47. As best shown in FIG. 4C, the transition 47 is rounded having a radius, $r_S$. The screw 40 has a proximal end 41a and a distal end 41b. The shaft 43 includes a threaded section 44 that is directly adjacent the distal end 41b of the screw 40, an outwardly tapered section 45, a stop section 45a, and a recessed section 46. The threaded section 44 is for engaging with internal threads 69 (shown in FIG. 7) in the implant 60 to hold the two-piece abutment 10 on the implant 60.

Moving along the shaft 43 from the distal end 41b towards the proximal end 41a of the screw 40, the outwardly tapered section 45 leads into the recessed section 46. The outwardly tapered section 45 of the shaft 43 has an increasing diameter such that the diameter along the outwardly tapered section 45 of the shaft 43 increases towards the proximal end 41a of the screw 40. It is contemplated that a maximum diameter $d_M$ of the outwardly tapered section 45 of the shaft is between 1.5 percent and 2.5 percent greater than a maximum diameter $d_S$ of the recessed section 46 of the shaft 43. Similarly, it is contemplated that the maximum diameter $d_M$ of the outwardly tapered section 45 of the shaft 43 is between 0.5 mils and 2.5 mils greater than the maximum diameter $d_S$ of the recessed section 46 of the shaft 43. Preferably, the maximum diameter $d_M$ of the outwardly tapered section 45 of the shaft 43 is about 1 mil greater than the maximum diameter $d_S$ of the recessed section 46 of the shaft 43.

The stop section 45a is positioned directly between the outwardly tapered section 45 and the recessed section 46. The stop section 45a includes a relatively sharp decrease in diameter of the shaft 43. The stop section 45a can include a tapered surface that has an angle $\theta_S$ relative to the vertical axis. The angle $\theta_S$ can be between about 40 degrees and about 90 degrees. The stop section 45a is arranged along the shaft 43 of the screw 40 to prevent and/or inhibit the washer 50, that is positioned in the recessed section 46 of the shaft 43, from being removed from the screw 40, such as, for example, by being slid towards the distal end 41b of the shaft 43 and past the stop section 45a, the outwardly tapered section 45, and the threaded section 44. That is, once the washer 50 is slid along the shaft 43, from a distal end 41b towards a proximal end 41a, press fit over the outwardly tapered section 45 and past the stop section 45a, the washer 50 becomes stuck (e.g., laterally fixed) within the recessed section 46 of the shaft 43 between the head 42 and the stop section 45a.

Figure 5A:
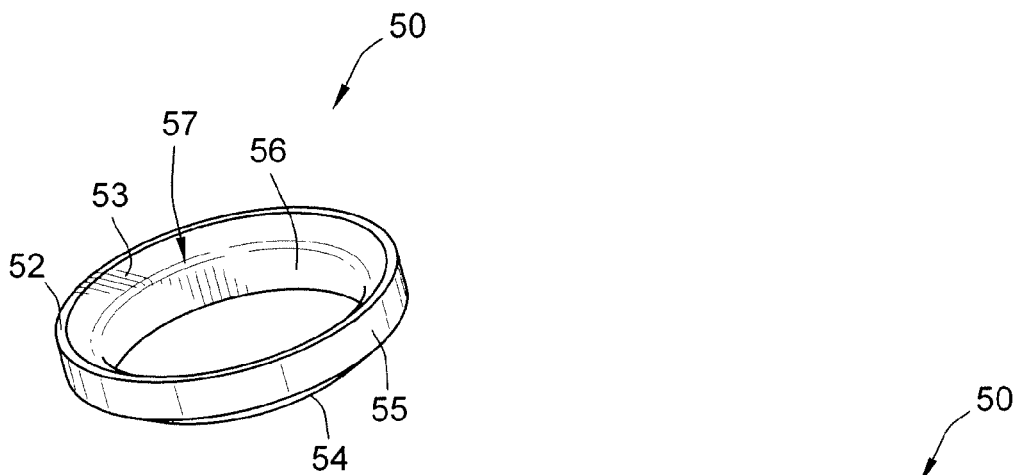
FIG. 5A is a perspective view of the washer of FIG. 1A.
Figure 5B:
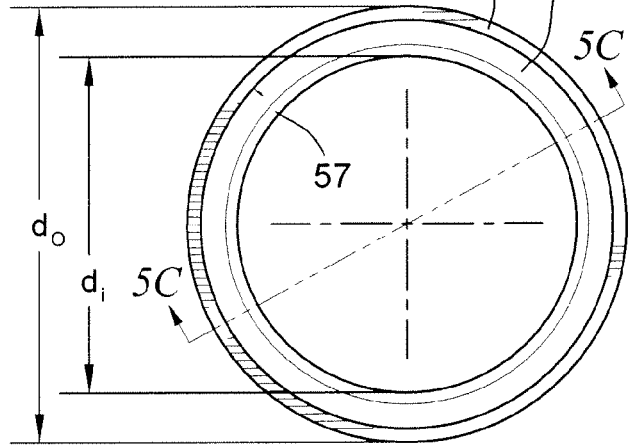
FIG. 5B is a top view of the washer of FIG. 5A.
Figure 5C:
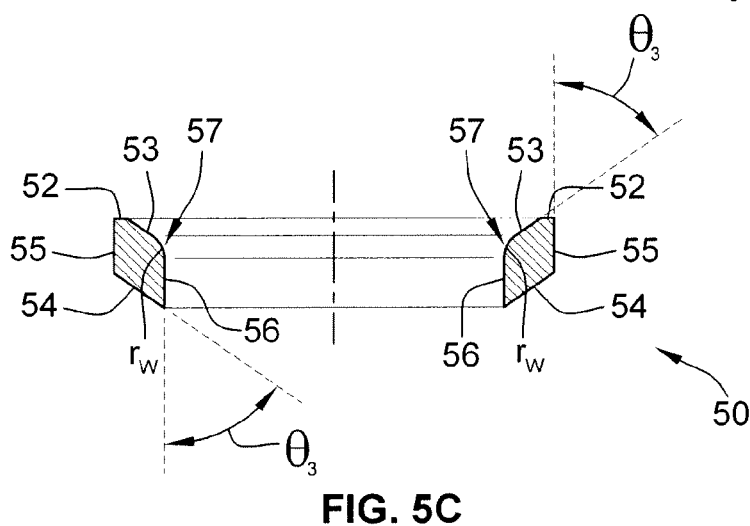
FIG. 5C is a side cross-sectional view of the washer of FIG. 5A.

Referring generally to FIGS. 5A-5C, the washer 50 is illustrated. The washer 50 has a top lip 52, an top tapered washer surface 53, a bottom tapered washer surface 54, an outer side surface 55, an inner side surface 56, and a transition surface 57. The top and bottom tapered washer surfaces 53, 54 each have an angle of $\theta_3$ relative to the vertical. $\theta_3$ can be a variety of angles, such as, for example, about 55 degrees.

It is contemplated that $\theta_3$ is larger than $\theta_1$ and $\theta_2$. For example, $\theta_3$ can be at least 20 percent greater than $\theta_1$ and $\theta_2$. For another example, $\theta_3$ can be at least 40 percent greater than $\theta_1$ and $\theta_2$. When a clinician installs the screw 40 by applying a torque to the screw head 42, the larger angles $\theta_3$ of the top and bottom tapered washer surfaces 53, 54, deform thereby causing the washer 50 to exert a spring-type force on the head 42 of the screw 40. This spring-type force on the head 42 of the screw 40 increases the preload of the screw 40. Additionally, the washer 50 decreases the friction between the second tapered head surface 42b of the screw 40 (FIG. 4A) and the tapered bore surface 29 of the prosthetic portion 20 (FIG. 3A), which also increases the preload of the screw 40. Such an increase in preload is advantageous as the greater preload results in an overall stronger coupling between the two-piece abutment 10 and the implant 60.

Where the tapered section 44 engages with the internal threads 69 of the implant 60 (FIG. 7) and a torque is applied to the head 42 of the screw 40, the washer 50 can deform in shape such that the angle $\theta_3$ is reduced. Specifically, the washer 50 is crushed and/or compressed between the second tapered head surface 42b of the screw 40 and the tapered bore surface 29 of the prosthetic portion 20 (best shown in FIG. 8). It is contemplated that the deformation of the washer 50 results in the reduction of the angle $\theta_3$ by at least 5 percent. For example, the angle $\theta_3$ can deform from being about 55 degrees to being about 35 degrees relative to the vertical.

As shown in FIGS. 5A-5C, the transition surface 57 is directly between the top tapered washer surface 53 and the inner side surface 56. The transition surface 57 is rounded having a radius, $r_W$. The transition surface 57 can be rounded so as to mate with the rounded transition 47 of the screw 40. The radius, $r_S$, of the transition 47 of the screw 40 is about twice the radius, $r_W$, of the transitional surface 57 of the washer 50. It is contemplated that such a ratio of radii ($r_S/r_W=2$) provides for a better connection between the washer 50 and the screw 40 when the screw 40 is attached to the implant 60. The ratio of radii also provides space between the top tapered washer surface 53 of the washer 50 and the second tapered head surface 42b of the screw head 42 for the washer 50 to deform during attachment of the two-piece abutment 10 to the implant 60.

An inner diameter $d_i$ of the washer 50 (FIG. 5C) is slightly smaller than the maximum diameter $d_M$ of the outwardly tapered section 45 of the screw 40 (FIG. 4C). As discussed above, such a relationship prevents the washer 50 from being removed (e.g., slid off) from the screw 40 once the washer 50 is press fit onto the screw 40, i.e., moved past the stop section 45a towards the proximal end 41a of the screw 40. That is, the washer 50 is stretched slightly as the washer 50 is press-fit over the outwardly tapered section 45 of the shaft 43. The inner diameter $d_i$ of the washer 50 is substantially equal to or slightly larger than a diameter of the threaded section 44 and/or the diameter $d_S$ of the recessed section 46 and the rest of the shaft 43 (between the threaded section 44 and the outwardly tapered section 45). Thus, the washer 50 is only press fit along the outwardly tapered section 45 of the shaft 43 of the screw 40.

It is contemplated that the maximum diameter $d_M$ of the outwardly tapered section 45 is about 1 mil greater than the inner diameter $d_i$ of the washer and/or about 1 mil greater than the diameter $d_S$ of the recessed section 46 of the shaft 43. It is further contemplated that the maximum diameter $d_M$ of the outwardly tapered section 45 is between 1 percent and 4 percent greater than the inner diameter $d_i$ of the washer 50 and/or between 1 percent and 4 percent greater than the diameter $d_S$ of the recessed section 46 of the shaft 43.

Referring to FIGS. 6 and 7, the two-piece abutment 10 is illustrated as being mating with the implant 60. The implant 60 includes an upper surface 65 for engaging the table 35 of the insert 30, and an internal bore 66 having at least one anti-rotational feature. As shown, the implant 60 includes a first anti-rotational feature 67 and a second anti-rotational feature 68 just below the first anti-rotational feature 67. The non-round section 32 of the insert 30 engages the first anti-rotational feature 67 on the implant 60. The second anti-rotational feature 68 may be used to drive the implant 60 into bone or to mate with other types of components.

After the two-piece abutment 10 is fitted in the correct position within the implant 60, the screw 40 can be inserted into the internal bore 28 of the prosthetic portion 20 and through the internal opening 38 (FIGS. 2A-2C) of the insert 30 to be mated with the internal threads 69 (FIG. 7) of the implant 60. As a clinician applies torque to the screw 40 (i.e., rotates the screw 40), the screw 40 further engages with the internal threads 69, which causes the screw 40 to translate vertically in a downward direction and increases the preload of the screw 40. The downward translation of the screw 40 causes the washer 50 (FIGS. 7 and 8) to deform between the second tapered head surface 42b of the head 42 of the screw 40 and the tapered bore surface 29 of the prosthetic portion 20.

Figure 8:
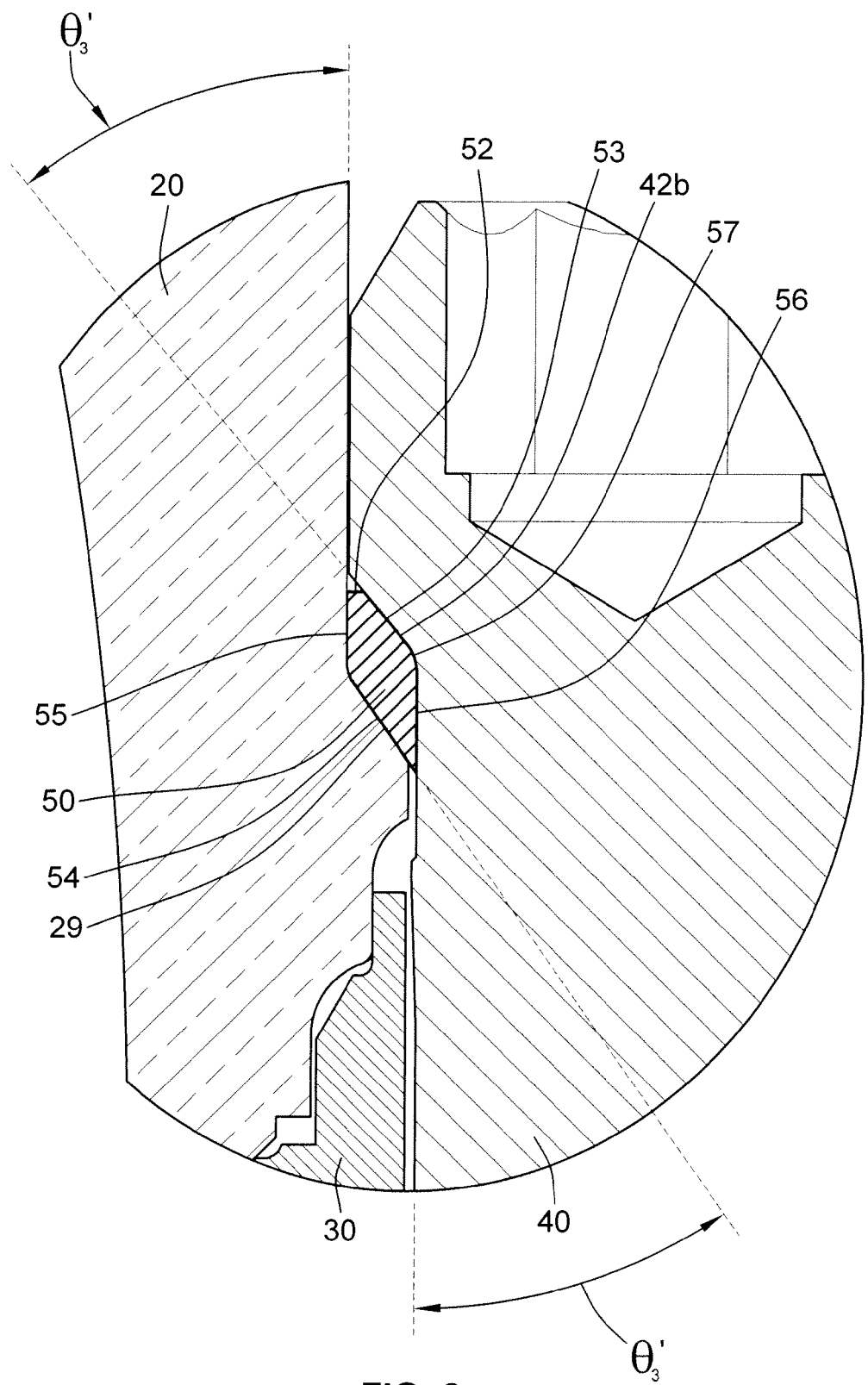
FIG. 8 illustrates a close-up view of section 8 in FIG. 7 illustrating the mating relationship of the screw, the washer, and the prosthetic portion of FIG. 1.

The deformed washer 50 is best shown in FIG. 8, which is an enlarged view of the engagement between the prosthetic portion 20, the screw 40, and the washer 50 after the screw 50 is installed and pretensioned. As shown in FIG. 8, the angle $\theta_3$ (FIG. 5C) of the top tapered washer surface 53 is deformed to a smaller angle of $\theta_3'$ due to the installation and pretensioning process of the screw 40. Similarly, the angle $\theta_3$ (FIG. 5C) of the bottom tapered washer surface 54 is deformed to a smaller angle of $\theta_3'$. It is contemplated that $\theta_3'$ is substantially the same as, or similar to, $\theta_1$ and $\theta_2$.

The present disclosure contemplates the use of the disclosed screw 40 and the disclosed washer 50 in combination with a variety of two-piece abutments (prosthetic portion and insert), such as, for example, the prosthetic portion and insert of the two-piece abutment disclosed in U.S. Published Patent Application 2009/0130629, entitled "Two-Piece Dental Abutment System," which is hereby incorporated by reference herein in its entirety.

Additionally, the present disclosure contemplates the use of the disclosed screw 40 and the disclosed washer 50 in combination with a variety of one-piece abutments, such as, for example, abutments that include a prosthetic portion without a separate and distinct insert. In such embodiments, the prosthetic portion is configured to directly couple to the implant via the screw 40 and the washer 50 without an insert positioned therebetween.

The washer 50 of the present disclosure is preferably made of titanium or titanium alloys, although it can be made of other biocompatible materials of sufficient properties to deform between the screw 40 and the prosthetic portion 20 as described herein. Accordingly, other exemplary materials include stainless steel, cobalt chromium alloys, gold alloys, and plastics.

The screw 40 of the present disclosure is preferably made of stainless steel with a gold plating, although it can be made of other biocompatible materials of sufficient properties to engage the dental implant 60 without deforming during usage. Accordingly, other exemplary materials include titanium or titanium alloys, cobalt chromium alloys, gold alloys, ceramics (e.g., alumina, zirconium), and stronger plastics such as polyether-ether-ketone ("PEEK").

The insert 30 of the present disclosure is preferably made of titanium or titanium alloys, although it can be made of other biocompatible materials of sufficient properties to engage the dental implant 60 without deforming during usage. Accordingly, other exemplary materials include stainless steel, cobalt chromium alloys, gold alloys, ceramics (e.g., alumina, zirconium), and stronger plastics such as polyether-ether-ketone ("PEEK").

The prosthetic portion 20 is comprised of a biocompatible material having sufficient properties to support a prosthesis located on its support section 22. As such, the prosthetic portion 20 can be made of metal, such as titanium, titanium alloy, stainless steel, cobalt chromium alloys, and gold alloys. Additionally, the prosthetic portion 20 can be made of a ceramic material, such as alumina or zirconium, which, unlike the darker shaded metals, has a lighter coloring and providing better aesthetics. The prosthetic portion 20 can also be made of a polymeric material, such as PEEK, which may be especially useful for temporary abutments.

The present disclosure contemplates the use of a prosthetic portion 20 having an asymmetrically arranged support region 22 around a central axis of the prosthetic portion 20 such that the two-piece abutment 10 can be used as an angled abutment. In practice, the angle and distance at which the supporting region 22 extends from the central axis 28a is varied in a kit of components such that a two-piece abutment 10 can be selected by the clinician so as to best fit the prevailing conditions in the patient's mouth.

The present disclosure contemplates the use of a single type of insert 30 with a plurality of prosthetic portions 20 comprised of different materials. For example, a titanium insert 30 may be included within a single kit that includes a plurality of prosthetic portions 20 comprised of different materials, such as a titanium prosthetic portion 20 and a ceramic prosthetic portion 20.

The prosthetic portion 20 (and possibly a portion of the insert 30) may be treated with a biocompatible coating through a process, such as anodizing, deposition, sputtering, or plating, to render that component a color that is better disguised under the gingival tissue. For example, the prosthetic portion 20 can be treated with a gold-colored or pink-colored titanium anodizing process or a titanium nitride coating.

The insert 30 and/or prosthetic portion 20 can also be treated with a biocompatible treatment process, such as anodizing, deposition, sputtering, plating, or ion implantation, to impart anti-microbial properties. For example, the surfaces can be treated with anti-microbial silver particles (e.g., nano-scale particles) or an antibiotic delivered by controlled resorbable materials adhered to the surface. Because of the need for maintaining a clean and stable environment at the seams of any mating components in the mouth, the surfaces on the table 35 of the insert 30 and the corresponding lowermost surface of the prosthetic portion 20 may be particularly in need of a treatment in accordance with these processes, especially anti-microbial silver particles.

Furthermore, the insert 30 and/or prosthetic portion 20 can be treated with a biocompatible coating, such as anodizing, deposition, sputtering, plating, or ion implantation, to aid in the gingival tissue healing process. For example, the surfaces can be treated with collagen, hydroxyapatite (e.g., nano-scale crystalline particles of hydroxyapatite), growth factors, and/or proteins.

While the top tapered washer surface 53 and the bottom tapered washer surface 54 are illustrated as each having the same angle of $\theta_3$ (FIG. 5C) and $\theta_3'$ (FIG. 8) relative to the vertical, the present disclosure contemplates that the angles of the top and bottom tapered washer surfaces 53, 54 can be different both prior to installation and/or after installation. For example, it is contemplated that the top tapered washer surface is 55 degrees and the bottom tapered washer surface is 60 degrees prior to installation and pretensioning of the screw 40. For another example, it is contemplated that the top tapered washer surface is 38 degrees and the bottom tapered washer surface is 42 degrees after installation and pretensioning of the screw 40.

Figure 9A:
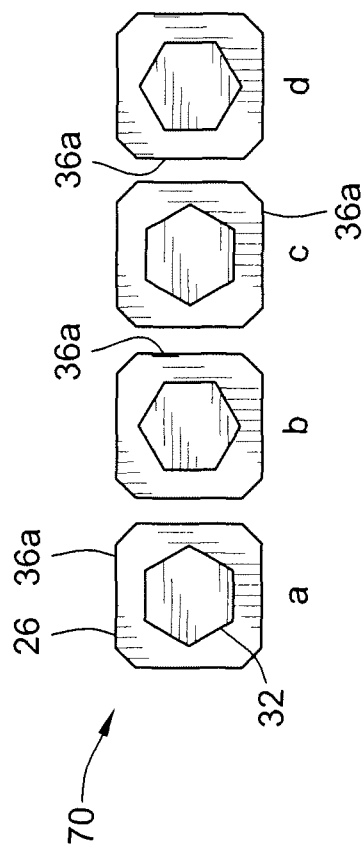
FIG. 9A illustrates possible anti-rotational orientations for a two-piece abutment relative to a hexagonal fitting of an implant.

Referring to FIG. 9A, a first set of angular positions 70 that is used with a two-piece abutment 10 having square-shaped non-round sections 26, 36 on the prosthetic portion 20 and on the insert 30. The anti-rotational feature 32 of the insert 30, which is the hexagonally shaped boss section below the table 35 of the insert 30 (FIG. 2A), is also shown.

In position "a" of FIG. 9A, there is a certain angular orientation of one surface of the anti-rotational feature 32 of the insert 30 to one surface of the non-round section 26 of the prosthetic portion 20 (and, thus, for the upper support section 22 of the prosthetic portion 20). If the insert 30 is rotated clockwise 90 degrees (while keeping prosthetic portion 20 in the same position) such that surface 36a on the non-round section 36 of the insert 30 is engaged on the right surface of the non-round section 26 of the prosthetic portion 20, then position "b" between the insert 30 and the prosthetic portion 20 is established. Similarly, if the insert 30 is again rotated clockwise 90 degrees, such that the surface 36a is engaged on the bottom surface of the non-round section 26 of the prosthetic portion 20, then the position "c" between the insert 30 and the prosthetic portion 20 is established. Finally, if the insert 30 is again rotated clockwise 90 degrees, such that the surface 36a is engaged on the left surface of the non-round section 26 of the prosthetic portion 20, then position "d" between the insert 30 and the prosthetic portion is established.

Accordingly, as illustrated in first set of angular positions 70 in FIG. 9A, there are four possible relative positions between one surface of the anti-rotational feature 32 of the insert 30 and the upper support region 22 of the prosthetic portion 20. However, two sets of positions (a & c; b & d) are duplicates of each other. Considering that the hexagonal anti-rotational feature 32 provides six possible final positions on the implant 60, the overall two-piece abutment 10 can provide up to twelve different mounting positions on the implant 60 (2 positions at the insert 30/prosthetic portion 20 interface multiplied by 6 positions of the hexagonal anti-rotational feature 32). This is important when the support region 22 is asymmetrically arranged around a central axis of the prosthetic portion 20 to create an angled abutment on the implant 60.

Figure 9B:
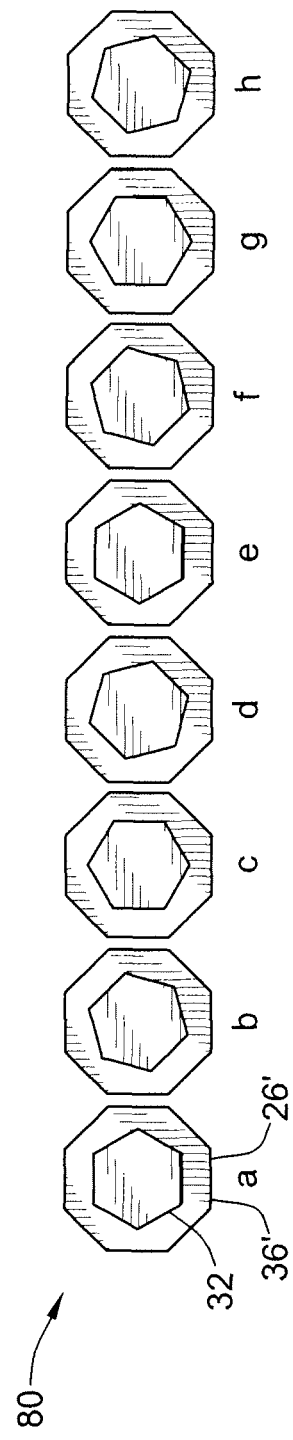
FIG. 9B illustrates possible anti-rotational orientations for a second two-piece abutment relative to a hexagonal fitting of an implant.

FIG. 9B illustrates a second set of angular positions 80 wherein the non-round section 26' of the prosthetic portion 20 and the non-round section 36' of the insert 30 are modified to have an octagonal shape as opposed to a square shape. Following the analysis set forth to the first set of angular positions 70 in FIG. 9A, there are eight possible positions for inserting the insert 30 into the prosthetic portion 20. Accordingly, there are eight possible angular configurations of the prosthetic portion 20 relative to the insert 30 with four sets of positions (a & e; b & f; c & g, d & h) being duplicates of each other. Considering that the hexagonal anti-rotational feature 32 provides six different positions on the implant 60, the overall two-piece abutment 10 can provide up to twenty-four different mounting positions on the implant 60 (4 positions at the insert 30/prosthetic portion 20 interface multiplied by 6 positions of the hexagonal anti-rotational feature 32).

In summary, FIGS. 9A and 9B illustrate that the two-piece abutment 10 provides for multiple abutment positions on the implant 60 with less variations in component manufacturing that is required. Rather than machining a single-piece angled abutment with two different variations for the position of the underlying hexagonal socket to fit on the implant in 12 ways, a single prosthetic portion 20 and a single insert 30 can provide the same result if a square brooch is used for the non-round sections 26, 36. And if an octagonal broach is used for the non-round sections 26, 36, a single prosthetic portion 20 and a single insert 30 can provide the same result as four angled abutments, each with a different position of the underlying hexagonal socket.

Additionally, inserts can be developed that include lower features for engagement with other types of mating features on implants, such as Morse tapers, or other non-round shapes.

Accordingly, the present disclosure contemplates a kit of components that includes a plurality of different inserts capable of mating with a plurality of different implants. Each of the inserts can be used with the same prosthetic portion 20. The kit also includes a plurality of different sizes and shapes of prosthetic portions 20 that mate with each type of insert, providing substantial variation for the resulting two-piece abutments.

It should be noted that the present disclosure contemplates a simple kit of components that can be used by the clinician for a temporary abutment prior to the placement of a permanent abutment on the implant. Often, such a temporary abutment may be placed on the implant after it has been installed with an "immediate loading" protocol. In this situation, the clinician would choose an insert 30 and an appropriately sized and shaped prosthetic portion 20 that will receive temporary material, such as acrylic, to provide the patient with an aesthetically pleasing prosthetic tooth mounted on the implant. The clinician would attach the insert 30 to the selected prosthetic portion 20 prior to the placement on the implant for use as a temporary abutment.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims. For example, the present invention contemplates kits having the inserts and prosthetic portions of the same general configuration, but different sizes to accommodate differently sized implants.

What is claimed is:

1. An Abutment system for use with a dental implant, the internal bore having a tapered bore surface;

a screw insertable through the internal bore and configure to engage threads of an internally threaded bore of the dental implant, the screw comprising a head and a shaft, the head including a tapered head surface, and the shaft including an outwardly tapered section that has an increasing diameter such that the diameter along the outwardly tapered section of the shaft increases towards the head of the screw, a maximum diameter of the outwardly tapered section of the shaft being no greater than a minimum diameter of the internal bore, and a washer configured to be positioned about the shaft of the screw, wherein, when the screw engages the dental implant, the washer is between the tapered head surface and the tapered bore surface such that a top washer surface directly engages with the tapered head surface and a bottom washer surface directly engages with the tapered bore surface, wherein the shaft further includes a threaded section, a recessed section, and a stop section between the outwardly tapered section and the recessed section.

2. The abutment system of claim 1, where the outwardly tapered section leads into the recessed section.

3. The abutment system of claim 1, wherein the washer is positioned about the recessed section, the washer having an inner diameter that is less than a maximum diameter of the outwardly tapered section of the shaft.

4. The abutment system of claim 3, wherein the washer is configured to be slid onto the shaft of the screw towards the head of the screw, past the threaded section and past the outwardly tapered section such that the washer is positioned within the recessed section of the shaft of the screw between the head and the stop section.

5. The abutment system of claim 4, wherein the washer is configured to be press-fitted over the outwardly tapered section of the shaft.

6. An abutment system for use with a dental implant, the abutment system comprising:
a prosthetic portion having an internal bore;
a screw insertable through the internal bore and configured to engage threads of an internally threaded bore of the dental implant, the screw comprising a head, a shaft, and a rounded transition between the head and the shaft, the rounded transition having a screw-head-transition radius; and
a washer including a top tapered washer surface, a bottom tapered washer surface, and a transition surface, the transition surface having a washer-transition radius, the screw-head-transition radius being about two times greater than the washer-transition radius.

7. The abutment system of claim 6, wherein the rounded transition of the screw provides space for the washer to deform.

8. The abutment system of claim 6, wherein the transition surface of the washer is directly adjacent to the top tapered washer surface.

9. The abutment system of claim 6, wherein the internal bore has a tapered bore surface with an angle of a degrees relative to a vertical axis parallel with the internal bore of the prosthetic portion and the head of the screw has a tapered head surface with an angle of substantially $\alpha$ degrees relative to the vertical axis parallel with the internal bore of the prosthetic portion.

10. The abutment system of claim 9, wherein the top tapered washer surface is configured to conformably engage with the tapered head surface of the head of the screw and the bottom tapered washer surface is configured to conformably engage with the tapered bore surface of the internal bore of the prosthetic portion.

11. The abutment system of claim 9, wherein the top and bottom tapered washer surfaces each have an angle of $\beta$ degrees relative to the vertical axis parallel with the internal bore of the prosthetic portion, and wherein $\beta$ is at least 20 percent greater than $\alpha$.

12. The abutment system of claim 11, wherein $\beta$ is at least 40 percent greater than $\alpha$.

13. The abutment system of claim 11, wherein $\alpha$ is about 35 degrees and $\beta$ is about 55 degrees.

14. The abutment system of claim 11, wherein the washer is configured to deform upon a torque being applied to the head of the screw such that the angle $\beta$ is reduced by at least 5 percent.

15. An abutment system for use with a dental implant, the abutment system comprising:
a prosthetic portion having an internal bore, the internal bore including a tapered bore surface having an angle of $\alpha$ degrees relative to a vertical axis parallel with the internal bore of the prosthetic portion;
a screw insertable through the internal bore and configured to engage threads of an internally threaded bore of the dental implant, the screw comprising a head and a shaft, the head including a tapered head surface having an angle of substantially $\alpha$ degrees relative to the vertical axis parallel with the internal bore of the prosthetic portion; and
a washer including a top tapered washer surface configured to conformably engage with the tapered head surface and a bottom tapered washer surface configured to conformably engage with the tapered bore surface, the top and bottom tapered washer surfaces each having an angle of $\beta$ degrees relative to the vertical axis parallel with the internal bore of the prosthetic portion, wherein the washer is configured to deform upon a torque being applied to the head of the screw such that the angle $\beta$ is reduced by at least 5 percent and wherein prior to the torque being applied to the head of the screw, $\beta$ is at least 20 percent greater than $\alpha$.

16. The abutment system of claim 15, wherein the washer is configured to exert an upward spring force on the head of the screw upon the torque being applied to the head of the screw.

17. The abutment system of claim 15, wherein prior to the torque being applied to the head of the screw, $\beta$ is at least 40 percent greater than $\alpha$.

18. The abutment system of claim 15, wherein $\alpha$ is about 35 degrees and $\beta$ is about 55 degrees.

19. The abutment system of claim 15, wherein the shaft comprises a proximal end and distal end, the proximal end of the shaft being coupled to the head, the shaft including a threaded section, an outwardly tapered section leading into a recessed section, and a stop section directly between the outwardly tapered section and the recessed section, the recessed section being directly between the head and the stop section, the outwardly tapered section having an increasing diameter such that the diameter along the outwardly tapered section of the shaft increases towards the head of the screw, the washer having an inner diameter that is less than a maximum diameter of the outwardly tapered section of the shaft.

* * * * *

UNITED STATES PATENT AND TRADEMARK OFFICE
CERTIFICATE OF CORRECTION

PATENT NO. : 9,717,571 B2
APPLICATION NO. : 14/516375
DATED : August 1, 2017
INVENTOR(S) : Goodman et al.

Page 1 of 1

It is certified that error appears in the above-identified patent and that said Letters Patent is hereby corrected as shown below:

In the Claims

In Column 10, Line 43, in Claim 1, delete "Abutment" and insert --abutment-- therefor In Column 10, Line 45, in Claim 1, delete "configure" and insert --configured-- therefor In Column 10, Line 66, in Claim 2, delete "where" and insert --wherein-- therefor In Column 11, Line 35, in Claim 9, delete "a" and insert --α-- therefor Signed and Sealed this
Sixteenth Day of July, 2019

Andrei Iancu
*Director of the United States Patent and Trademark Office*